United States Patent
Mulaveesala et al.

(10) Patent No.: US 11,039,089 B2
(45) Date of Patent: Jun. 15, 2021

(54) THERMAL IMAGING FOR IDENTIFYING A DEFECT IN A MATERIAL

(71) Applicant: INDIAN INSTITUTE OF TECHNOLOGY ROPAR, Punjab (IN)

(72) Inventors: Ravibabu Mulaveesala, Punjab (IN); Vanita Arora, Punjab (IN); Geetika Dua, Punjab (IN)

(73) Assignee: INDIAN INSTITUTE OF TECHNOLOGY ROPAR, Punjab (IN)

( * ) Notice: Subject to any disclaimer, the term of this patent is extended or adjusted under 35 U.S.C. 154(b) by 0 days.

(21) Appl. No.: 16/830,131

(22) Filed: Mar. 25, 2020

(65) Prior Publication Data
US 2020/0314357 A1    Oct. 1, 2020

(30) Foreign Application Priority Data
Mar. 27, 2019   (IN) .............................. 201911012086

(51) Int. Cl.
| | |
|---|---|
| C12Q 1/686 | (2018.01) |
| H04N 5/33 | (2006.01) |
| G01J 5/04 | (2006.01) |
| G01J 5/00 | (2006.01) |

(52) U.S. Cl.
CPC ................ *H04N 5/33* (2013.01); *G01J 5/046* (2013.01); *G01J 2005/0077* (2013.01)

(58) Field of Classification Search
CPC .................................. H04N 5/33; G01J 5/046
See application file for complete search history.

(56) References Cited

U.S. PATENT DOCUMENTS

| | | | | |
|---|---|---|---|---|
| 7,692,698 | B2* | 4/2010 | Hara ...................... | H04N 5/378 348/241 |
| 2011/0216223 | A1* | 9/2011 | Nakamura ............. | H04N 5/361 348/231.99 |
| 2019/0191120 | A1* | 6/2019 | Ikedo ..................... | H04N 5/379 |
| 2019/0226008 | A1* | 7/2019 | Whitman ............. | C12Q 1/6823 |
| 2019/0279349 | A1* | 9/2019 | Morino .................... | G06T 7/97 |
| 2020/0107877 | A1* | 4/2020 | Koblish ................ | A61B 5/743 |

* cited by examiner

*Primary Examiner* — Jonathan R Messmore
(74) *Attorney, Agent, or Firm* — Nguyen Tarbet LLC

(57) ABSTRACT

The present subject matter proposes a novel pulse compression favourable non-periodic thermal wave imaging that enhance the energy concentration capabilities and defect detection sensitivity and resolution in comparison with presently used pulse compression favourable thermal wave imaging approaches. This is due to most of the supplied energy is concentrated in the main lobe and very less energy will be redistributed to side lobes by the proposed Complimentary Golay coded excited thermal wave imaging.

14 Claims, 9 Drawing Sheets

THERMAL IMAGING FOR IDENTIFYING A DEFECT IN A MATERIAL

CROSS-REFERENCE TO RELATED APPLICATIONS AND PRIORITY

The present application claims benefit from Indian Complete Patent Application No. 201911012086 filed on 27 Mar. 2019, the entirety of which is hereby incorporated by reference.

TECHNICAL FIELD

The present disclosure in general relates to a system and a method of thermal imaging of a material. More particularly, the present disclosure further relates to identify a defect in the material by thermal imaging in a non-destructive manner.

BACKGROUND

During the recent years, Carbon Fibre Reinforced Plastic (CFRP) materials have gained progressive interest in various industrial applications as these composite materials offer several benefits over metals, mainly high strength and stiffness to weight ratios, good fatigue tolerance and superior corrosion resistance. Despite these inherent advantages, there are concerns regarding occurrence of delaminates, inclusions, surface and sub-surface defects during the manufacturing stage. Thus, an effective way of identifying the defects is required.

In recent years, infrared thermographic techniques have gained wide acceptance for identifying defects of various solid materials due to the inherent merits of thermographic techniques such as non-contact, fast, quantitative and suitability for the safe field inspection. Conventionally used pulse compression based aperiodic thermal wave imaging such as frequency modulated thermal wave imaging, digitized frequency modulated thermal wave imaging, Barker coded thermal wave imaging are the approaches to identify defect with test resolution and sensitivity. However, these techniques have limited sensitivity in identifying the defect in the material.

SUMMARY

It is to be understood, that this application is not limited to the particular systems, and methodologies described, as there can be multiple possible embodiments, which are not expressly illustrated, in the present disclosure. It is also to be understood that the terminology used in the description is for describing the particular versions or embodiments only, and is not intended to limit the scope of the present application. This summary is provided to introduce concepts related to a system and a method of thermal imaging for identifying a defect in a material this summary is not intended to identify essential features of the claimed subject matter nor is it intended for use in determining or limiting the scope of the claimed subject matter.

In one implementation, a method of thermal imaging for identifying a defect in a material is illustrated. In order to identify a defect in a material, in one aspect, a processor may receive a thermal response of a material. Further, the processor may generate a reconstructed zero mean temperature from the thermal response based on removal of a mean rise in a temperature. Furthermore, the processor may generate a first pulse compressed thermographic single pixel profile based on the reconstructed zero mean temperature. In another aspect, the processor may generate a second pulse compressed thermographic single pixel profile based on the reconstructed zero mean temperature. In one another aspect, the processor may generate a third pulse compressed thermographic value based on a sum of an auto-correlation function of the first pulse compressed thermographic single pixel profile and the second pulse compressed thermographic single pixel profile. In yet another aspect, the processor may identify the defect of the material from the third compressed thermographic value.

In another implementation, a system of thermal imaging for identifying a defect in a material is illustrated. In one embodiment, the system comprises a memory, a processor coupled to the memory. The processor receives a thermal response of a material. Further, the processor may generate a reconstructed zero mean temperature from the thermal response based on removal of a mean rise in a temperature. Furthermore, the processor may generate a first pulse compressed thermographic single pixel profile based on the reconstructed zero mean temperature. In another aspect, the processor may generate a second pulse compressed thermographic single pixel profile based on the reconstructed zero mean temperature. In one another aspect, the processor may generate a third pulse compressed thermographic value based on a sum of an auto-correlation function of the first pulse compressed thermographic single pixel profile and the second pulse compressed thermographic single pixel profile. In yet another aspect, the processor may identify the defect of the material from the third compressed thermographic value.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to refer like features and components.

DETAILED DESCRIPTION

Figure 1:
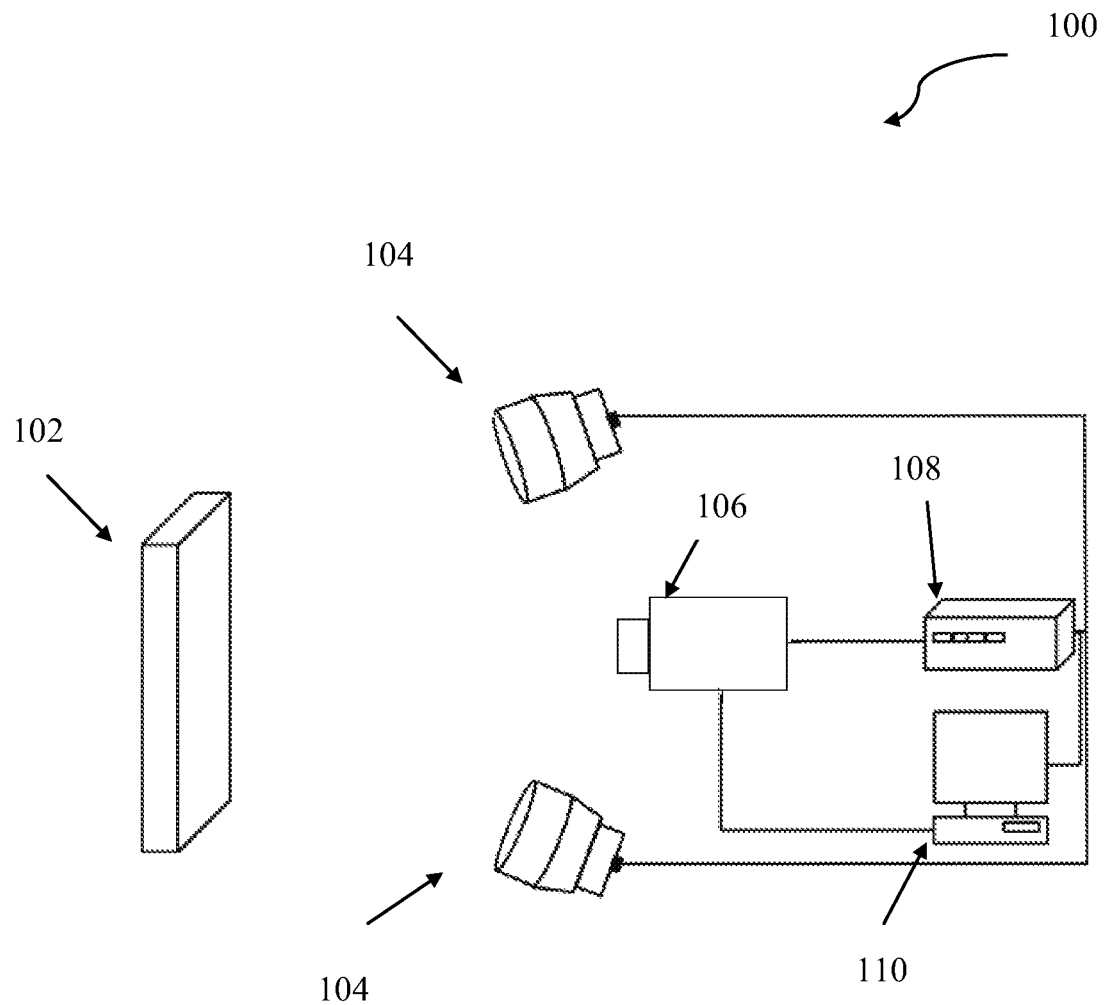
FIG. 1 illustrates an experimental set up, in accordance with an embodiment of the present subject matter.

Some embodiments of the present disclosure, illustrating all its features, will now be discussed in detail. The words "comprising", "including", and other forms thereof, are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a", "an" and "the" include plural references unless the context clearly dictates otherwise. Although any systems and methods similar or equivalent to those described herein can be used in the practice or testing of embodiments of the present disclosure, a system and a method of thermal imaging for identifying a defect in a material is now described. The disclosed embodiment of a system and a method of thermal imaging for identifying a defect in a material are merely exemplary of the disclosure, which may be embodied in various forms.

Various modifications to the embodiment will be readily apparent to those skilled in the art and the generic principles herein may be applied to other embodiments. However, one of ordinary skill in the art will readily recognize that the present disclosure a method for of thermal imaging for identifying a defect in a material is not intended to be limited to the embodiments illustrated, but is to be accorded the widest scope consistent with the principles and features described herein.

As described above, there are some limitations in the conventional approach for identifying a defect in a material. In order to improve the test sensitivity for identifying the defect in the material, conventionally, several methods are used such as pulse compression based aperiodic thermal wave imaging such as frequency modulated thermal wave imaging, digitized frequency modulated thermal wave imaging, Barker coded thermal wave imaging. However, a significant supplied energy is redistributed into the side lobes that limits the sensitivity in identifying the defect in the material. Thus, there is need to overcome the limitation.

In one implementation, a system and a method of thermal imaging for identifying a defect in a material is illustrated. In order to identify a defect in a material, in one aspect, a processor may receive a thermal response of a material. Further, the processor may generate a reconstructed zero mean temperature from the thermal response based on removal of a mean rise in a temperature. Furthermore, the processor may generate a first pulse compressed thermographic single pixel profile based on the reconstructed zero mean temperature. In another aspect, the processor may generate a second pulse compressed thermographic single pixel profile based on the reconstructed zero mean temperature. In one another aspect, the processor may generate a third pulse compressed thermographic value based on a sum of an auto-correlation function of the first pulse compressed thermographic single pixel profile and the second pulse compressed thermographic single pixel profile. In yet another aspect, the processor may identify the defect of the material from the third compressed thermographic value.

In one embodiment there may include an advantage that includes the sensitivity for identifying the defect in the material is improved by concentrating most of the supplied energy into a main lobe with reduced leakage into side lobes.

Now, referring to FIG. 1, various elements of an experimental set up in order to identify a defect in a material 102 by thermal imaging is illustrated in accordance with an embodiment of the present subject matter. In one embodiment, the experimental set 100 comprises a material 102, a halogen lamp 104, an infrared camera 106, a system 108, and a computer 110 for display. In one aspect, the halogen lamp 104 may be two. In one aspect, the material 102 may be a mild steel or a carbon fibre reinforced polymer. In one aspect, the halogen lamp 104 illuminates the material 102. In another aspect, the halogen 104 lamp may be kept at a distance of about 1 Meter from the material 102 in order to illuminate the material 102 uniformly. The halogen lamp 104 may act as a heat source of 1 KW. Further, an intensity of the halogen lamp 104 is modulated by the system 108 in accordance with each one of a chosen pair of 8-bit complementary coded excitations for a duration of 100 seconds. In one another aspect, the infrared camera 106 captures an image of the material 102 after the material 102 is illuminated. Further, the captured image is received by the system 108.

Figure 2:
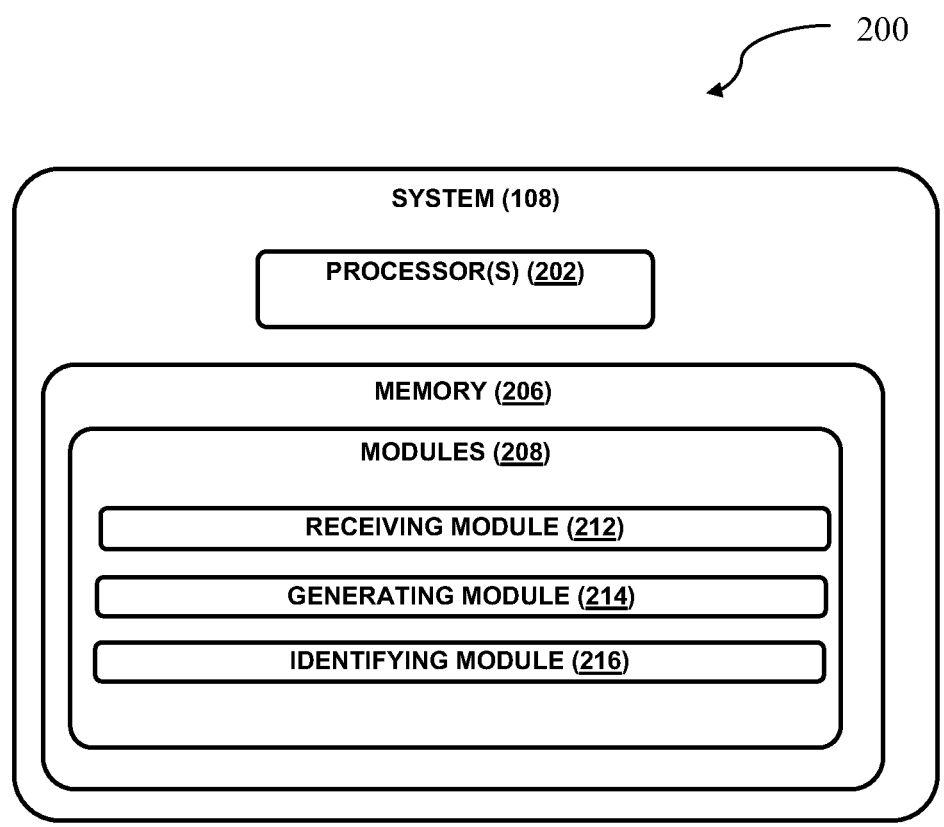
FIG. 2 illustrates a system of thermal imaging for identifying a defect in a material, in accordance with an embodiment of the present subject matter.

Now, referring to FIG. 2, the system 108 of thermal imaging for identifying a defect in the material 102 with an embodiment of the present subject matter is illustrated. In one embodiment, the system 108 may include at least one processor 202, and a memory 206. The at least one processor 202 may be implemented as one or more microprocessors, microcomputers, microcontrollers, digital signal processors, central processing units, state machines, logic circuitries, and/or any devices that manipulate signals based on operational instructions. Among other capabilities, at least one processor 202 may be configured to fetch and execute computer-readable instructions stored in the memory 206.

The memory 206 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 206 may include modules 208.

The modules 208 may include routines, programs, objects, components, data structures, and the like, which perform particular tasks, functions or implement particular abstract data types. The modules 208 may include a receiving module 212, a generating module 214 and an identifying module 216. The functioning of all the modules in the system 108 is described as below:

Receiving Module 212

In one embodiment, the receiving module receives the captured infrared image of the material 102. In one aspect, the image is captured by the infrared camera 106.

Generating Module 214

In one embodiment, the processor 202 generates a reconstructed zero mean temperature from the thermal response based on removal of a mean rise in a temperature. In one aspect, the processor 202 further generates a first pulse compressed thermographic single pixel profile based on the reconstructed zero mean temperature. The processor 202 furthermore generates a second pulse compressed thermographic single pixel profile based on the reconstructed zero mean temperature. In one aspect, the processor 202 generates a third pulse compressed thermographic value based on a sum of the first pulse compressed thermographic single pixel profile and the second pulse compressed thermographic single pixel profile.

Figure 3:
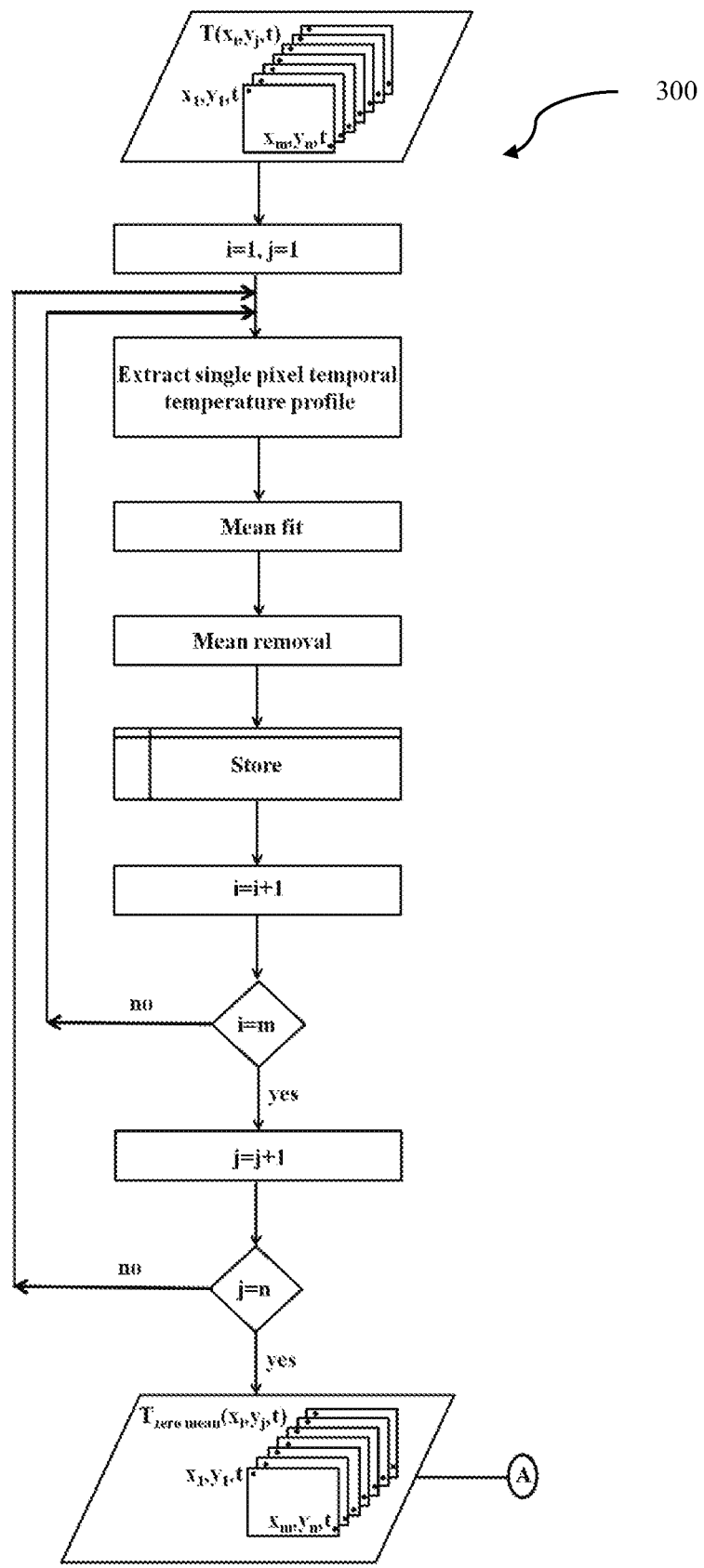
FIG. 3 illustrates a flowchart of generating a reconstructed zero mean temperature, in accordance with an embodiment of the present subject matter.

In another embodiment, the reconstructed zero mean temperature is generated from the thermal response based on removal of a mean rise in a temperature. In one aspect, the reconstructed zero mean temperature may be generated by extracting a single pixel temperature profile from the thermal response, further, the zero mean single pixel profile is generated based on applying a linear fit function on the single pixel temperature profile. Furthermore, the zero mean single pixel profile is generated. In one aspect, the reconstructed zero mean temperature is generated from the zero mean single pixel profile. In one another aspect, the reconstructed zero mean temperature may be carried out by flowing steps (as shown in FIG. 3):

T ($x_i$, $y_j$, t) denotes the captured thermal response. Here, 'i' and T refer to pixel sequence along the x and y dimension respectively, t signifies the frame number.

From this captured response, the single pixel temperature profile (i.e for i=1,j=1, over the frames) is extracted.

On this extracted temporal thermal profile, the linear fit function is applied to reconstruct the zero mean single pixel profile, which is then stored.

In similar manner, all the pixel profiles are processed one by one by incrementing 'i' and 'j' until i=m and j=n, where m, n are the dimensions of each frame.

Further, the zero mean temperature data (Tzeromean ($x_i$,$y_j$,t)) is reconstructed from the stored profiles.

Figure 4:
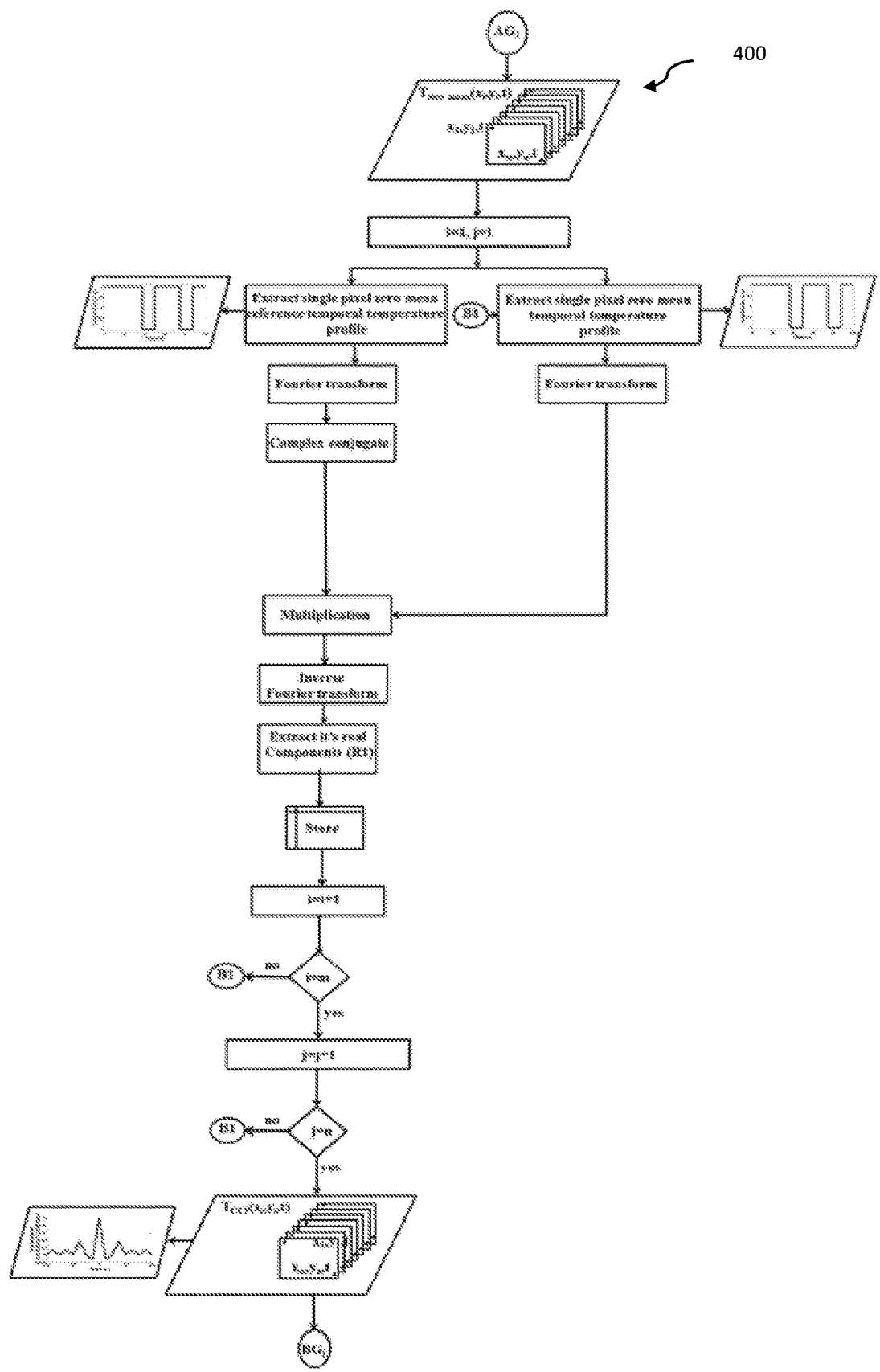
FIG. 4 illustrates a flowchart of generating a first pulse compressed thermographic single pixel profile, in accordance with an embodiment of the present subject matter.

In yet another embodiment, the first pulse compressed thermographic single pixel profile is generated based on the reconstructed zero mean temperature. In one aspect, the first pulse compressed thermographic single pixel profile may be a golay sequence one. In another aspect, the first pulse compressed thermographic single pixel profile may be generated by extracting one pixel profile from the reconstructed zero mean temperature, further, the Fourier transform of the one pixel profile is generated. Furthermore, a complex conjugate of the one pixel profile is generated. The second pixel profile is extracted from the reconstructed zero mean temperature. In addition, the Fourier transform of the second pixel profile is generated. In one aspect, the first multiplied value is generated based on based on multiplying the one pixel profile and the second pixel profile. In one implementation, an inverse Fourier transform of the first multiplied value is generated. In another aspect, the first pulse compressed thermographic single pixel profile is generated from the inverse Fourier transform of the first multiplied value by extracting real components of the first multiplied value. In one aspect, generating the first pulse compressed thermographic single pixel profile based on the reconstructed zero mean temperature may be carried out by following steps (as shown in FIG. 4):

T zeromean ($x_i$,$y_j$,t) here denotes the reconstructed zero mean temperature distribution profile.

From this data, extract one pixel profile (mainly pixel at any non-defective location) and take it as a reference profile.

Apply Fourier Transform on this extracted reference profile and then compute the complex conjugate of it.

On the other side, extract the second pixel profile from the reconstructed zeromean temperature profile starting with i=1, j=1, apply Fourier Transform on it and then multiply this data with processed reference data.

Further, take the inverse transform of the multiplied data. Extract and store the real components of inverse transformed data. This is the first pulse compressed single pixel profile.

In similar manner, extract each pixel from the zeromean data by incrementing 'i' and T, till i=m and j=n, apply Fourier transform and multiply with the complex conjugate of the Fourier transform of reference data.

At last, from the stored pulse compressed single pixel profiles, complete pulsed compressed data for the Golay sequence 1 (TCC1($x_i$,$y_j$,t)) is reconstructed for further processing.

In another embodiment, the second pulse compressed thermographic single pixel profile is generated based on the reconstructed zero mean temperature. In one aspect, the second pulse compressed thermographic single pixel profile may be a golay sequence two. In another aspect, the second pulse compressed thermographic single pixel profile may be executed by extracting the third pixel profile from the reconstructed zero mean temperature, further, a Fourier transform of the third pixel profile is generated. In one aspect, a complex conjugate of the third pixel profile is generated. A fourth pixel profile is generated from the reconstructed zero mean temperature. In one aspect, the Fourier transform of the fourth pixel profile is generated. In addition, the second multiplied value is generated based on multiplying the third pixel profile and the fourth pixel profile. In yet another aspect, an inverse Fourier transform of the second multiplied value is generated. In one implementation, the second pulse compressed thermographic single pixel profile is generated from the inverse Fourier transform of the second multiplied value by extracting real components of the second multiplied value.

Figure 5:
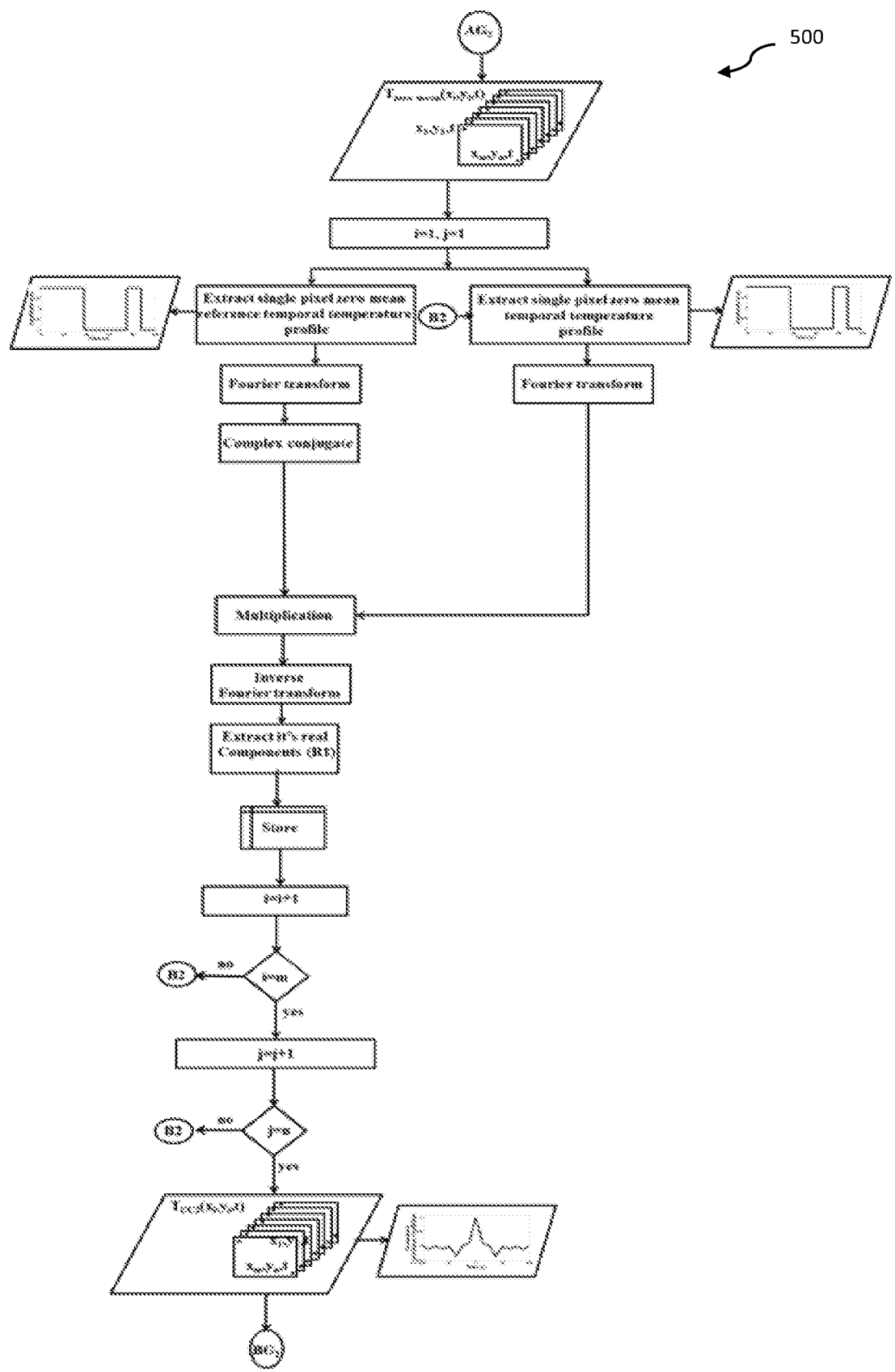
FIG. 5 illustrates a flowchart of generating a second pulse compressed thermographic single pixel profile, in accordance with an embodiment of the present subject matter.

In one implementation, the second pulse compressed thermographic single pixel profile generated based on the reconstructed zero mean temperature may be carried out by following steps (as shown in FIG. 5):

Tzeromean($x_i$,$y_j$,t) here denotes the reconstructed zeromean temperature distribution profile.

From this data, extract third pixel profile (mainly pixel at any non-defective location) and take it as a reference profile.

Apply Fourier Transform on this extracted reference profile and then compute the complex conjugate of it.

On the other side, extract fourth pixel profile from the zeromean temperature profile starting with i=1, j=1, apply Fourier Transform on it and then multiply this data with processed reference data.

Further, take the inverse transform of the multiplied data. Extract and store the real components of inverse transformed data. This is the second pulse compressed single pixel profile.

In similar manner, extract each pixel from the zeromean data by incrementing 'i' and T, till i=m and j=n, apply Fourier transform and multiply with the complex conjugate of the Fourier transform of reference data.

At last, from the stored pulse compressed single pixel profiles, complete pulsed compressed data for the Golay sequence 2 (TCC2($x_i$,$y_j$,t)) is reconstructed for further processing.

In another embodiment, the third pulse compressed thermographic value is generated based on a sum of an autocorrelation function of the first pulse compressed thermographic single pixel profile and the second pulse compressed thermographic single pixel profile. In one aspect, the third pulse compressed thermographic value may be generated by extracting a first single pixel pulse compressed profile from the first pulse compressed thermographic single pixel profile and a second single pixel pulse compressed profile from the second pulse compressed thermographic single pixel profile. Further, the third pulse compressed thermographic value is generated based on the addition of the first single pixel pulse compressed profile and the second pixel pulse compressed profile.

Figure 6:
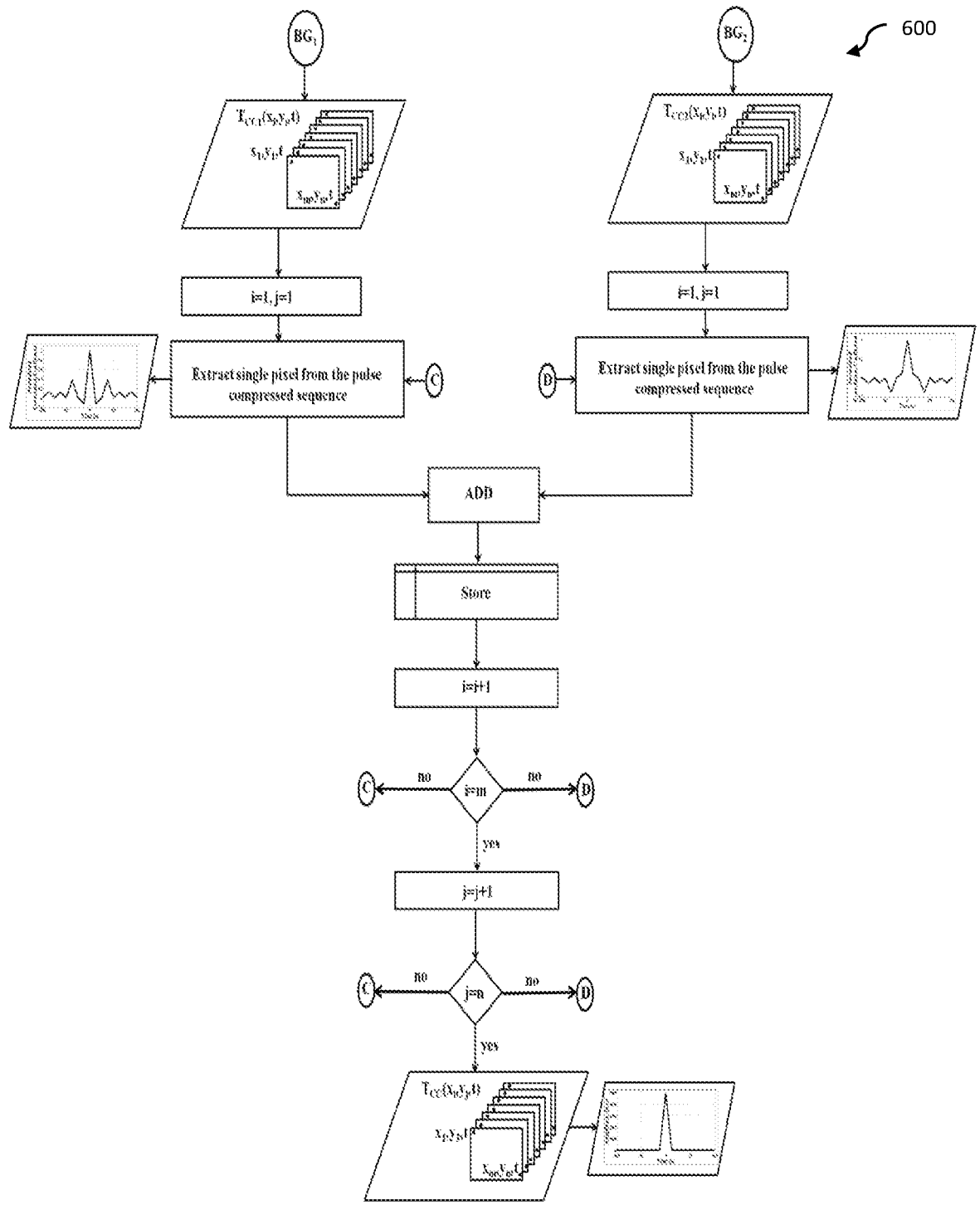
FIG. 6 illustrates a flowchart of generating a third pulse compressed thermographic single pixel profile, in accordance with an embodiment of the present subject matter.

In one aspect, the third pulse compressed thermographic value generated based on a sum of the first pulse compressed thermographic single pixel profile and the second pulse compressed thermographic single pixel profile may be carried out by following steps (as shown in FIG. 6):

TCC1(xi,yj,t) and TCC2(xi,yj,t) are the first pulse compressed thermographic single pixel profile and the second pulse compressed thermographic single pixel respectively.

Extract a first single pixel pulse compressed profile and a second single pixel pulse compressed profile from the first pulse compressed thermographic single pixel profile and the second pulse compressed thermographic single pixel profile by taking i=1, j=1.

Add both the profiles and store.

Further, increment i and j and repeat the procedure, till i=m and j=n.

Next, from the stored profiles, extract the third pulse compressed thermographic value with zero side lobes.

Identifying Module 216

A defect is identified of the material 102 from the third pulse compressed thermographic value.

In subsequent embodiments, different examples of the present subject matter is described in detail. In one example, complementary coded thermal wave imaging scheme for thermal non-destructive testing and evaluation is described. In one implementation, during the recent years, Carbon Fiber Reinforced Plastic (CFRP) materials have gained progressive interest in various industrial applications as these composite materials offer several benefits over metals, mainly high strength and stiffness to weight ratios, good fatigue tolerance and superior corrosion resistance. Despite these inherent advantages, there are concerns regarding occurrence of delaminates, inclusions, surface and sub-surface defects during the manufacturing stage. This requires an effective non-destructive evaluation technique in order to detect buried defects and to maintain the overall long-term durability of these materials. InfraRed Non-Destructive Testing (IRNDT), if compared to other NDT methods, is rapidly gaining wide acceptance as a whole-field, non-intrusive and non-contact evaluation technique for the characterization of composite materials. The basic principle of active IRNDT consists of thermally exciting the sample to be inspected, using an external heat source. The heat propagation is affected by the presence of defects causing thermal variations over the sample, which can be monitored using an infrared camera. Further analyzing this thermal response by suitable data-processing scheme leads to extraction of surface and sub-surface details.

Pulse Thermography (PT), Lock-in Thermography (LT), and Pulse Phase Thermography (PPT) are the widely used conventional IRNDT techniques. Detection of deeper sub-surface features in composite materials by means of PT demands high peak power heat sources and also the captured thermal map is affected by non-uniform heating and surface emissivity variations. LT uses mono-frequency sinusoidal thermal excitation and derives the phase information from the observed thermal response that is insensitive to inhomogeneous excitation and local emissivity variations. In order to resolve defects located at different depths inside the test sample, LT requires repetition of the test at different frequencies, which makes it, time-consuming process. The experimentation in PPT is similar to PT and the data analysis carried out is similar to LT. Among the various aperiodic thermal excitations such as Frequency Modulated Thermal Wave Imaging (FMTWI), Digitized Frequency Modulated Thermal Wave Imaging (DFMTWI) Quadrature Frequency Modulated Thermal Wave Imaging (QFMTWI) [27], Barker Coded Thermal Wave Imaging (BCTWI), the earlier three methods (FMTWI, DFMTWI, QFMTWI) are superior for their continuous depth scanning capabilities and the later scheme (BCTWI) even it fails to provide continuous depth scanning capabilities during the active heating still it is preferable due to its better pulse compression properties obtained from adopting a suitable post processing on the captured temporal temperature distribution Due to its inherent properties of correlation based post processing scheme and it's energy concentration capabilities of the supplied energy into the main lobe of the compressed pulse with a little amount of the supplied energy distributed to its side lobes makes it as a superior and retains its usage over FMTWI, DFMTWI and QFMTWI techniques. However still an excitation technique, which can further improves pulse compression properties of these aperiodic excitation schemes will be an advantageous for achieving improved test sensitivity and resolution to detect surface or sub-surface defects in the test material. This present work describes a novel experimental implementation of Golay Coded Thermal Wave Imaging (GCTWI) using complementary coded pair thermal excitation. The capabilities of the proposed technique are evaluated on a CFRP sample having flat-bottom holes by using correlation based pulse compression approach.

In another embodiment, the thermal model used for non-destructive inspection using GC TWI consists of imposing Golay complementary coded pair thermal stimulus on the test sample. The resultant temperature profile over the sample is recorded using an infrared camera. Golay complementary codes are a pair of equal length sequences that have the property of generating zero sidelobes when the autocorrelation functions of individual sequences are algebraically added. Each code in complementary Golay code pair is having length N=2M, where M is a positive integer. Let a=(a0, a1, . . . , aN−1) and b=(b0, b1, . . . , bN−1) be a sequence of length N such that (ai,bi) {+1,−1} i.e. all code elements are bi-phase. The 8-bit complementary coded pair thermal excitation employed in the present study is represented (not shown)

The auto-correlation function of sequence a and b is defined as:

$$R_a(k) = \sum_{i=0}^{N-k-1} a_i a_{i+k} \quad 0 \leq k \leq N-1 \quad (1)$$

and $$R_b(k) = \sum_{i=0}^{N-k-1} b_i b_{i+k} \quad 0 \leq k \leq N-1 \quad (2)$$

Figure 7:
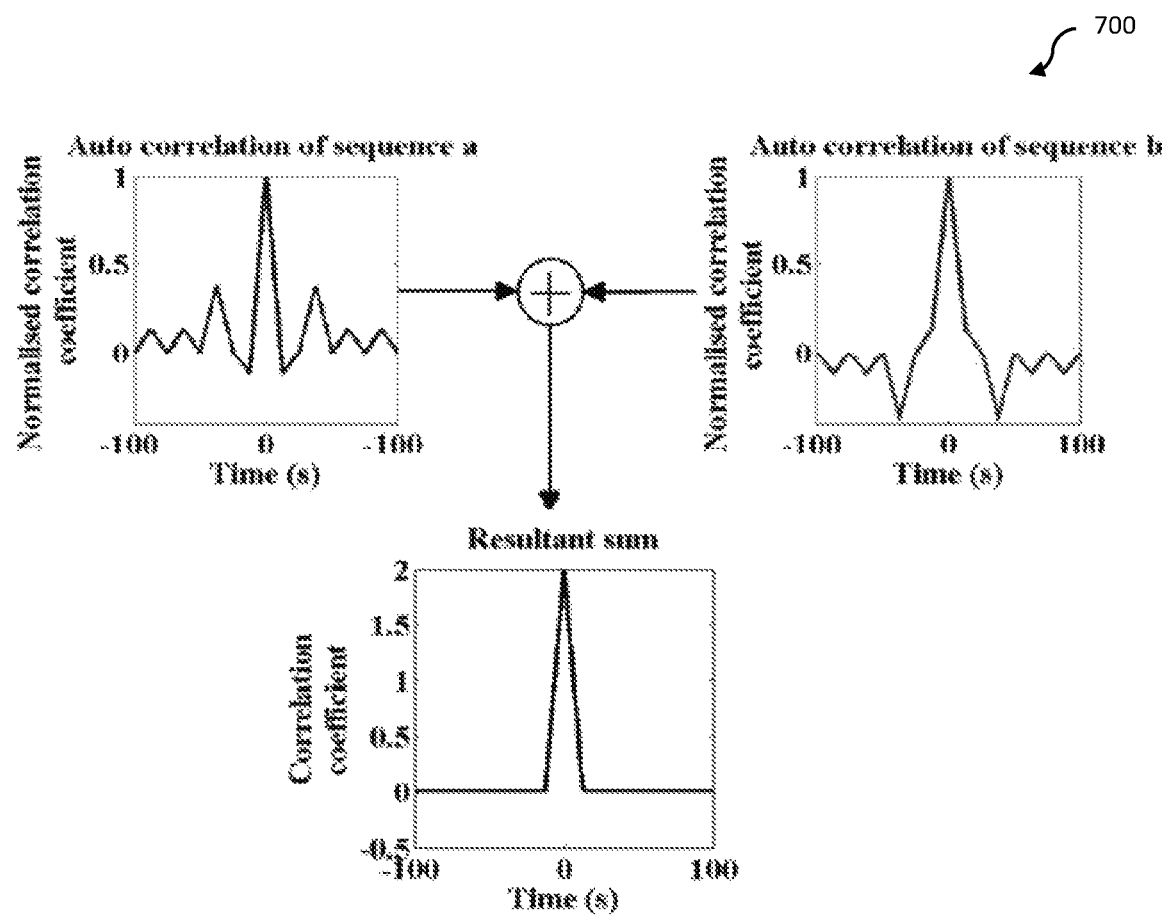
FIG. 7 illustrates Auto-correlation functions of complementary code pair and their resultant sum, in accordance with an embodiment of the present subject matter.

Theoretically, the slim of these two alto-correlation functions is zero for any time shift k except k=0 as given below:

$$R_a(k) + R_b(k) = \begin{Bmatrix} 0 & k \neq 0 \\ 2N & k = 0 \end{Bmatrix} \quad (3)$$

i.e. addition of these two correlation functions leads to the complete removal of side lobes from the compressed pulse as illustrated in FIG. 7.

This addition results in a compressed pulse with a peak of double the sequence length and zero sidelobes, hence provides a significant enhancement in the Signal-to Noise Ratio (SNR) by making use of low peak power heat sources. The choice of sequence length depends on the test time constraints and optimum expected response.

The thermal energy propagation through a thermally excited solid can be described by Fourier's one-dimensional heat equation in the absence of any heat source and sink inside the sample which can be written as $$\frac{\partial^2 T(x,t)}{\partial x^2} = \frac{1}{\alpha} \frac{\partial T(x,t)}{\partial t} \qquad (4)$$

where $T(x,t)$ is the temperature at a given spatial location x at a given time t and a is the thermal diffusivity of the sample being inspected. The proposed 8-bit complementary coded pair thermal stimulus can be expressed below as the combination of shifted step functions (u):

For sequence a:

For sequence $a$: (5)

$$f_a(t) = P_0 \sum_{i=1}^{6} (-1)^{n_i} u(t - a_i \tau)$$

where $n_i = 0, 1, 2, 3, 4, 5; \quad a_i = 0, 3, 4, 6, 7, 8.$
and $P_0$ is the peak excitation power.

For sequence $b$: (6)

$$f_b(t) = P_0 \sum_{i=1}^{4} (-1)^{n_i} u(t - a_i \tau)$$

where $n_i = 0, 1, 2, 3; \quad a_i = 0, 3, 6, 7.$

The solution to heat equation (4) for the propagation of coded pair heat flux through a semi-infinite solid under boundary conditions (x=0, T(x=0,t)=applied heat stimulus and x directs to infinity, T—ambient temperature) and initial condition (T(x,t=0)=0) can be derived as:

For sequence $a$: (7)

$$T_a(x,t) = \frac{4\beta P_0 (\sqrt{\alpha})^2}{K\sqrt{\pi}\, x^2} \sum_{i=1}^{6} (-1)^{n_i} (t - a_i \tau)^{3/2} e^{-\frac{x^2}{4\alpha(t - a_i \tau)}}$$

For sequence $b$: (8)

$$T_b(x,t) = \frac{4\beta P_0 (\sqrt{\alpha})^2}{K\sqrt{\pi}\, x^2} \sum_{i=1}^{4} (-1)^{n_i} (t - a_i \tau)^{3/2} e^{-\frac{x^2}{4\alpha(t - a_i \tau)}}$$

The addition of auto-correlation of these obtained temperature profiles provides a compressed pulse with much of the energy concentrated in the main lobe and hence leads to better defect resolution by using even low peak power heat sources. Additionally, removal of side lobes improves the test sensitivity.

In the present investigation, a rectangular shaped (151*341 mm) (not shown) CFRP sample with 4.2 mm thickness containing blind holes and metallic inclusions, is considered. The test sample contains two groups of defects having various diameters kept at the same depth; group 1 contains a, b, c & d defects kept at 1.6 mm depth and group 2 contains e, f, g, h & i defects kept at 2.16 mm depth, from the front surface of the sample. Defects f, h and i (inclusions) are introduced as metallic backing of copper covered steel (not shown). In the experimental set up (as shown in FIG. 1) the thermal excitation source consists of two halogen lamps each of 1 KW power driven by the system 108 in accordance with the complementary coded signal for a duration of 100 s. These lamps are kept at a distance about 1 m from the CFRP sample to illuminate it uniformly. For the detection of thermal waves, an infrared camera having 320*256 pixel resolution is used. Acquisition of thermal data over the sample is carried at a frame rate of 25 Hz. Exemplary embodiments discussed above may provide certain advantages and applications, these advantages and applications may include the following.

The dc component in the captured thermal map is removed by polynomial fitting. The correlation coefficient between the mean removed resultant temporal thermal profiles of each pixel with the chosen non-defective pixel is obtained individually for both code d sequences. These two correlations are algebraically added leading to a compressed pulse with peak of double the magnitude of individual code.

A sequence of correlation sum images for the proposed complementary coded excitation scheme is presented (not shown). The scales are adjusted to attain maximum thermal contrast for the chosen images in order to enhance the visibility of defects. From the obtained results, it is clear that even for the blind holes having less lateral dimensions, the thermal contrast over the blind holes (detectability) is significantly higher than that of the metallic inclusions. This explains the detection capabilities of correlation sum images for different thermal effusively defects hidden inside the material, which may help in the classification of defects.

In order to quantitatively validate the detection capabilities of the proposed approach, Signal to Noise Ratio (SNR) of defects is taken into consideration and is calculated as:

$$SNR_{(dB)} = 20\log \frac{\text{Mean of the defective area} - \text{Mea of the sound area}}{\text{Standard deviation of the sound area}} \qquad (9)$$

The obtained SNR values for the considered defects, i.e. blind hole (a) and metallic inclusion (h) having same lateral dimensions is illustrated in Figure observed that the correlation sum leads to better SNR values compared to individual codes for both types of defects.

In yet another embodiment, complementary coded excited thermal wave imaging technique for infrared non-destructive testing and evaluation of a steel material is described. In one implementation, InfraRed Thermography (IRT) is one of the widely used effective imaging methods which allows to inspect the object for finding out the surface and subsurface anomalies in a fast and remote manner in various industries such as aeronautical, aerospace, bio-medical, civil, electrical and mechanical engineering. Active infrared thermography relies on the application of pre-defined thermal stimulus onto the test object to generate significant temperature gradient between defective and sound regions. GCTWI technique employs 8-bit binary complementary coded heat stimulus for thermal NDT and E. The complementary code sequence comprise a pair of equal finite length series having the property that the number of pairs of similar elements with any given separation in one series is equal to the number of pairs of dissimilar elements with the same separation in the other.

The reason for choosing complementary code pair as a thermal stimulus for IRT lies in the fact that this code suppresses the amplitude of side-lobes to zero. The autocorrelation functions of individual codes have the side-lobes equal in magnitude but opposite in sign. When these auto-correlation functions are added, it results in a single auto-correlation main-lobe with the peak of 2N (where N is the code sequence length) and zero side-lobes and hence the obtained SNR is improved. Increasing the sequence length leads to better SNR value, but also increase the experimentation time. So, a suitable sequence length is to be selected for optimum response by taking sensitivity and resolution into consideration. The present work considers 8-bit binary Golay complementary code heat stimulus. Each code in complementary Golay code pair is having length N=2M, where M is a positive integer. Let a=(a0, a1, . . . , aN−1) and b=(b0, b1, . . . , bN−1) are the code sequences, each of length N such that (ai,bi) {+1,−1(0)} i.e. all sequence elements in these codes are bi-phase (not shown).

The auto-correlation function of sequence a and b is defined as [17,18]:

$$R_a(k) = \sum_{i=0}^{N-k-1} a_i a_{i+k} \quad 0 \leq k \leq N-1 \quad (1)$$

and $$R_b(k) = \sum_{i=0}^{N-k-1} b_i b_{i+k} \quad 0 \leq k \leq N-1 \quad (2)$$

Theoretically, the sum of two auto-correlation functions is zero for any time shift k except k=0 as given below [17,18]:

$$R_a(k) + R_b(k) = \begin{Bmatrix} 0 & k \neq 0 \\ 2N & k = 0 \end{Bmatrix} \quad (3)$$

i.e. addition of these two correlation functions results in a single auto-correlation function with a peak of twice the sequence length having zero side lobes. This property leads to theoretically complete removal of side lobes from the compressed pulse as presented in FIG. 7.

To test the applicability of the proposed approach, a mild steel sample (not shown) of size 12.5×10.5×0.974 cm is taken into consideration. The sample contains six flat bottom hole defects each of diameter 1 cm located at various depths inside it, (not shown). The sample thickness is 0.974 cm.

As shown in the experimental set up in FIG. 1, two halogen lamps each of 1 KW are kept at a distance about 1 m from the sample to illuminate it uniformly. The intensity of these lamps is modulated by the system 108 in accordance with each one of the chosen pair of 8-bit complementary coded excitation for duration of 100 s. The infrared camera is arranged at a location of one meter from the sample to capture the temporal temperature distribution over the sample at a frame rate of 25 Hz. The mean rise in temperature profile during the active heating is removed by proper polynomial fit from the captured thermographic sequence. For each and individual mean removed coded sequence, the correlation coefficient between temporal temperature profile of each pixel with the chosen reference non-defective pixel is obtained. The auto correlation sequences of both complementary codes are added up to result a peak of twice the magnitude of individual code.

In another embodiment, sandwich structures are increasingly deployed in many industrial applications due to their high strength to weight ratio, good corrosion resistance, superior thermal insulating and energy absorption properties. Non-destructive evaluation of the structural integrity is essential for the quality assurance during the manufacturing and in-service phases. Among the modern-day Non-Destructive Testing and Evaluation (NDT and E) methodologies, InfraRed Thermography (IRT) is a technique with growing importance due to its abilities to inspect surface and sub-surface details in a fast, reliable, remote and quantitative manner. Active IRT is based on exciting the test object using a heat source, followed by monitoring the surface temperature distribution. To enhance the defect visualization, post-processing techniques are applied onto the recorded thermal data. Many IRT approaches have been developed in the literature based on the type of thermal stimulus and processing method. Pulse Thermography (PT), Lock-in Thermography (LT), and Pulse Phase Thermography (PPT) are the most employed techniques. However, these classical thermographic techniques have some limitations as the requisition of high peak power heat sources in pulse based techniques and long experimentation time in LT. In order to find a way to overcome these limitations, Frequency Modulated Thermal Wave Imaging (FMTWI), Quadrature Frequency Modulated Thermal Wave Imaging (QFMTWI), Digitized version of FMTWI (DFMTWI) and Barker Coded Thermal Wave Imaging (BCTWI) techniques have been proposed in recent years. This work intends to present an application of InfraRed Thermography (IRT) concerning the use of 8-bit binary Golay complementary coded thermal stimulus to evaluate the integrity of a sandwich structure.

This technique is based on the application of Golay complementary coded heat stimulus onto the test object. The complementary code consists of a pair of code sequences having a valuable property that the sum of their auto-correlation functions results in a compressed pulse with a peak of twice the sequence length and zero side lobes. This property allows complete removal of side lobes from the compressed pulse. The obtained compressed pulse improves the defect detection capabilities and permits the use of low peak power heat sources. Individual Golay sequences have relatively flat spectra. The signal to noise ratio of a Golay sequence can be shown to be bounded by its length. However, longer code lengths increase the experimentation time. So based on the test time constraints, a suitable code length is to be selected for optimum response by taking sensitivity and resolution into consideration. The present work considers binary Golay complementary code thermal excitation of length. The applied thermal energy propagates into the test specimen by diffusion and can be described by one-dimensional heat equation in the absence of any heat source and sink inside the specimen as $$\frac{\partial^2 T(x,t)}{\partial x^2} = \frac{1}{\alpha} \frac{\partial T(x,t)}{\partial t} \quad (1)$$

where T(x,t) is the temperature at a given spatial location x and at a given time t and α is the thermal diffusivity of the specimen. The applied 8-bit complementary coded pair stimulus can be expressed as the combination of step functions given by:

For sequence $a$:

$$f_a(t) = P_0 \sum_{i=1}^{6} (-1)^{n_i} u(t - a_i \tau) \tag{2}$$

where $n_i = 0, 1, 2, 3, 4, 5$; $a_i = 0, 3, 4, 6, 7, 8$.
and $P_0$ is the peak excitation power.

For sequence $b$:

$$f_b(t) = P_0 \sum_{i=1}^{4} (-1)^{n_i} u(t - a_i \tau) \tag{3}$$

where $n_i = 0, 1, 2, 3$; $a_i = 0, 3, 6, 7$.

The solution to equation (1) for a semi-infinite solid on the application of boundary conditions (x=0, T(x=0,t)=T0(constant temperature) and x directs to infinity, T—ambient temperature) and initial condition (T(x,t=0)=0) given by Carslaw and Jaeger (p. 60 of [10]) is as follows:

$$T(x, t) = T_0 \text{erfc}\left(\frac{x}{2\sqrt{\alpha t}}\right) \tag{4}$$

As the imposed complementary coded pair excitation consists of a combination of time shifted step functions. The solution is first extracted for a step function and then the same approach is applied for all the time shifted step functions of both the complementary coded sequences. The flux of heat at the surface of the object is given by:

$$f_1(t) = -K \frac{\partial T(x, t)}{\partial x} \tag{5}$$

where K is the thermal conductivity of the material. Step excitation (P0 u(t)) causes a constant flux over the surface at x=0, given as:

$$f_2(t) = \beta P_0 u(t) \text{erfc}\left(\frac{x}{2\sqrt{\alpha t}}\right) \tag{6}$$

$$T(x, t) = -\frac{1}{K} \int_x^{\infty} f_2(t) dx \tag{7}$$

Substituting value of f:(f):

$$T(x, t) = -\frac{1}{K} \int_x^{\infty} \beta P_0 \text{erfc}\left(\frac{x}{2\sqrt{\alpha t}}\right) dx$$

As $$i^n \text{erfc}(x) = \int_x^{\infty} i^{n-1} \text{erfc}(x) dx,$$

so the above equation reduces to:

$$T(x, t) = -\frac{2\beta P_0 \sqrt{\alpha t}}{K} i\text{erfc}\left(\frac{x}{2\sqrt{\alpha t}}\right) \tag{8}$$

Simplifying further using $$i\text{erfc}(x) = \frac{1}{\sqrt{\pi}} e^{-x^2} - x\text{erfc}(x) \text{ and}$$

$$\text{erfc}(x) = \frac{e^{-x^2}}{\sqrt{\pi}} \left(\frac{1}{x} - \frac{1}{2x^3} + \frac{3}{4x^5} \ldots \right)$$

and neglecting higher order terms of x (x5), the obtained solution for unit step excitation can be expressed as:

$$T(x, t) = \frac{4\beta P_0 (\sqrt{\alpha})^3}{K\sqrt{\pi} x^2} (\sqrt{t})^3 e^{\left(-\frac{x^2}{4\alpha t}\right)} \tag{9}$$

Applying the same approach for all the shifted step excitation functions of both coded sequences as follows: For sequence a:

$$f_{a_2}(t) = \beta P_0 \text{erfc}\left(\frac{x}{2\sqrt{\alpha t}}\right) \tag{10}$$

$$\{u(t) - u(t - 3\tau) + u(t - 4\tau) - u(t - 6\tau) + u(t - 7\tau) - u(t - 8\tau)\}$$

For sequence b:

$$f_{b_2}(t) = \beta P_0 \text{erfc}\left(\frac{x}{2\sqrt{\alpha t}}\right) \{u(t) - u(t - 3\tau) + u(t - 6\tau) - u(t - 7\tau)\} \tag{11}$$

The temperature response over the object for the stimulation given in equation (10) and (11) is obtained as:

For sequence a: (12)

$$T_a(x, t) = \frac{4\beta P_0 (\sqrt{\alpha})^3}{K\sqrt{\pi} x^2} \begin{bmatrix} (\sqrt{t})^3 e^{\left(-\frac{x^2}{4\alpha t}\right)} - \\ (\sqrt{t-3\tau})^3 e^{\left(-\frac{x^2}{4\alpha(t-3\tau)}\right)} + \\ (\sqrt{t-4\tau})^3 e^{\left(-\frac{x^2}{4\alpha(t-4\tau)}\right)} - \\ (\sqrt{t-6\tau})^3 e^{\left(-\frac{x^2}{4\alpha(t-6\tau)}\right)} + \\ (\sqrt{t-7\tau})^3 e^{\left(-\frac{x^2}{4\alpha(t-7\tau)}\right)} - \\ (\sqrt{t-8\tau})^3 e^{\left(-\frac{x^2}{4\alpha(t-8\tau)}\right)} \end{bmatrix}$$

$$T_a(x, t) = \frac{4\beta P_0 (\sqrt{\alpha})^3}{K\sqrt{\pi} x^2} \sum_{i=1}^{6} (-1)^{n_i} (t - a_i \tau)^{3/2} e^{-\frac{x^2}{4\alpha(t-a_i\tau)}}$$

-continued

For sequence b:

$$T_b(x, t) = \frac{4\beta P_0(\sqrt{\alpha})^3}{K\sqrt{\pi} x^2} \begin{bmatrix} (\sqrt{t})^3 e^{\left(-\frac{x^2}{4\alpha}\right)} - \\ (\sqrt{t-3\tau})^3 e^{\left(-\frac{x^2}{4\alpha(t-3\tau)}\right)} + \\ (\sqrt{t-6\tau})^3 e^{\left(-\frac{x^2}{4\alpha(t-6\tau)}\right)} - \\ (\sqrt{t-7\tau})^3 e^{\left(-\frac{x^2}{4\alpha(t-7\tau)}\right)} \end{bmatrix} \quad (13)$$

$$T_b(x, t) = \frac{4\beta P_0(\sqrt{\alpha})^2}{K\sqrt{\pi} x^2} \sum_{i=1}^{4} (-1)^{n_i} (t - a_i \tau)^{3/2} e^{-\frac{x^2}{4\alpha(t-a_i\tau)}}$$

The sample used in this study is realized by bonding a Glass Fibre Reinforced Fibre Polymer (GFRP) sheet of 5.1 mm thickness on one side of 30.8 mm thick wooden block. The other side of the core is comprised of 5.1 mm thick Carbon Fibre Reinforced Fibre Polymer (CFRP) sheet. Disbonds of different sizes are inserted at different locations within the sample FIG. 1 shows the experimental setup used for the present study. Two halogen lamps are kept at a distance about 1 m from the sample to illuminate the sample uniformly. The intensity of these lamps is modulated by the system 108 in accordance with a pair of complementary coded excitation for a duration of 100 s. The infrared camera is arranged at a location to capture the temporal thermal history over the sample at a frame rate of 25 Hz. The mean rise in thermal profile during the active heating is removed by proper polynomial fit. For both code sequences, the correlation coefficient between mean removed temporal thermal profiles of each pixel with the chosen reference non-defective pixel is then obtained individually. These two correlations are summed up resulting in a peak of twice the magnitude of individual code. This presents the series of correlation sum images obtained onto CFRP and GFRP facet respectively (not shown). The scales are adjusted so that the maximum thermal contrast is obtained for the chosen images in order to enhance the visibility of disbonds. The presence of disbonds can be clearly distinguished in the obtained images.

In another implementation, coded thermal wave imaging technique for infrared non-destructive testing and evaluation is described. In one implementation, Infrared Thermography (IRT) is a valuable tool in thermal non-destructive testing and evaluation community for inspection of various solid materials and to identity their surface and sub-surface anomalies. Defect detection capabilities of IRT can be realized either in passive or in active approach. In passive thermography, the infrared radiation emitted from the test object is measured under ambient conditions. However, passive approach fails to provide information for the defects located deep inside the test specimen as they provides insufficient thermal contrast over the defective regions to distinguish from the sound area. Whereas in active approach, an external thermal stimulus is applied onto the test object to induce relevant thermal contrasts, especially for the defects located deep inside the test object of smaller lateral dimensions. The defect detection sensitivity of IRT test, depends on the distinguishing of variation in the surface thermal profile over the test object at defect and sound regions; the greater the thermal contrast, the better will be the defect detection sensitivity of the test. These temperature contrast variations are acquired using Infrared camera and further explored using suitable post-processing technique to enhance the sub-surface defects details.

Among popular active IRT methods, Pulse Thermography (PT) and Lock-in Thermogarphy (LT) are the commonly used techniques. These conventional techniques do have potential limitations. PT requires high peak power heat sources in order to obtain considerable thermal contrast and also the observed thermal data is affected by non-uniform heating and surface emissivity variations. Long experimentation time and limited test resolution are the major drawbacks of LT.

In attempts to overcome the limitations of high peak power requirements of pulse based thermographic techniques and long experimentation times of single frequency modulated (fixed thermal wavelength inside the test specimen) lock-in thermography for detecting defects located at various depths of different lateral dimensions, various non-periodic modulated transient thermal wave imaging techniques such as Frequency Modulated Thermal Wave Imaging (FMTWI). Quadratic Frequency Modulated Thermal Wave Imaging (QFMTWI), Digitized Frequency Modulated Thermal Wave Imaging (DFMTWI), Barker Coded Thermal Wave Imaging (BCTWI), etc. have been suggested in the literature. The present paper aims to explore the defect detection capabilities of a novel thermal wave imaging processing approach for recently proposed Golay complementary coded heat stimulus for testing and evaluation of steel and carbon fibre reinforced polymer samples. The considered excitations are pair of complementary codes having the property that the sum of their individual auto-correlation functions leads to a compressed pulse with theoretically no side-lobe. This is due to the autocorrelation functions of the two code sequences which completely cancel each other everywhere except at zero shift, where they constructively add to produce a compressed pulse with amplitude 2N (where N is the code length). A mild steel sample having flat bottom hole defects and CFRP with flat bottom holes along with inclusions as sub-surface defects are examined using the proposed approach. The proposed approach implemented a 8-bit binary complementary Golay Coded Thermal Wave Imaging (GCTWI) technique by exciting the test sample with a 8 bit Golay coded heat stimulus (not shown). The complementary code pair consists of equal finite length sequences having a valuable property that the sum of auto-correlation of individual codes vanishes at all non-zero integer delays resulting in a sidelobe free compressed pulse having magnitude of twice the length of the sequence. Increasing the sequence length further leads to better Signal to Noise Ratio (SNR) value, but also increase the inspection time. So, suitable code length is to be selected for optimum response by taking test sensitivity and resolution into consideration. Each code in complementary Golay code pair is having length N=2M, where M is a positive integer. Let a=(a0, a1, . . . , aN−1) and b=(b0, b1, . . . , bN−1) are the code sequences, each of length N such that (ai,bi)∈{+1,−1(0)} i.e. all sequence elements in these codes are bi-phase (not shown).

$$R_a(k) = \sum_{i=0}^{N-k-1} a_i a_{i+k} \quad 0 \leq k \leq N-1 \quad (1)$$

$$R_b(k) = \sum_{i=0}^{N-k-1} b_i b_{i+k} \quad 0 \leq k \leq N-1 \quad (2)$$

Theoretically the sum of two auto-correlation functions is zero for oily time shift k except k=0 as below [16,17]:

$$R_a(k) + R_b(k) = \begin{Bmatrix} 0 & k \neq 0 \\ 2N & k = 0 \end{Bmatrix} \quad (3)$$

i.e. addition of these two correlation functions results in a single auto-correlation function with a peak of twice the sequence length having zero side lobes. This property leads to theoretically complete removal of side lobes from the compressed pulse as presented in FIG. 8. The applied 8-bit Golay complementary coded pair thermal excitation can be expressed as combination of step functions as:
For sequence a:

$$f_a(t) = P_0 \sum_{i=1}^{6} (-1)^{n_i} u(t - a_i \tau) \quad (4)$$

where $n_i = 0, 1, 2, 3, 4, 5$; $a_i = 0, 3, 4, 6, 7, 8$.

and $P_0$ is the peak excitation power.
For sequence b:

$$f_b(t) = P_0 \sum_{i=1}^{4} (-1)^{n_i} u(t - a_i \tau) \quad (5)$$

where $n_i = 0, 1, 2, 3$; $a_i = 0, 3, 6, 7$.

The thermal response over the object for the stimulation given in equation (4) and (5) is obtained as [16,17]:

For sequence a: (6)

$$T_a(x, t) = \frac{4\beta P_0(-\sqrt{\alpha})^3}{K\sqrt{\pi} x^2} \sum_{i=1}^{6} (-1)^{n_i} (t - a_i\tau)^{3/2} e^{-\frac{x^2}{4\alpha(t-a_i\tau)}}$$

For sequence b: (7)

$$T_b(x, t) = \frac{4\beta P_0(\sqrt{\alpha})^3}{K\sqrt{\pi} x^2} \sum_{i=1}^{4} (-1)^{n_i} (t - a_i\tau)^{3/2} e^{-\frac{x^2}{4\alpha(t-a_i\tau)}}$$

Figure 8:
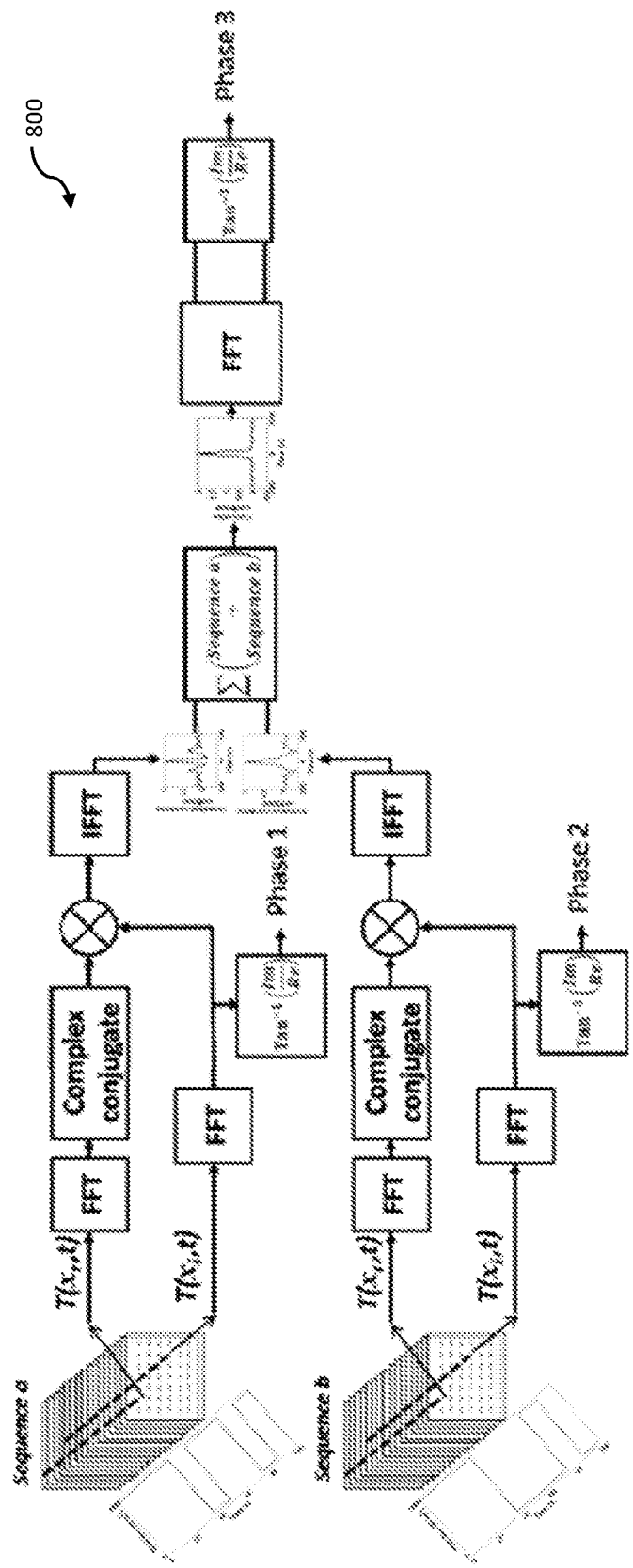
FIG. 8 illustrates complementary Golay coded thermal wave imaging approach, in accordance with an embodiment of the present subject matter.

Further, the conventional Fourier transform approach has been adopted on the obtained individual correlation functions of the sequence a (Ra(k)) and b (Rb(k)) and their resultant sum (Phase 1, Phase 2 and Phase 3 of FIG. 8 respectively). In this approach, one-dimensional Fourier Transform (FT) is applied on the captured temporal thermal profile of each pixel f(x) (where x is the index in the image sequence) as follows:

$$F(u) = \frac{1}{N} \sum_{n=0}^{N-1} f(x) e^{\left[\frac{-j2\pi ux}{N}\right]} = R(u) + jI(u) \quad (8)$$

$$\phi(u) = \tan^{-1}\left(\frac{I(u)}{R(u)}\right) \quad (9)$$

Experimental setup in FIG. 1 used for the present study for testing the mild steel as well as CFRP specimens is as shown in FIG. 1. Two halogen lamp heat sources of each of 1 KW are kept at a distance of about 1 m from the test object to illuminate it uniformly. The intensity of these lamps is modulated by the system 108 in accordance with each one of the chosen pair of 8-bit complementary coded excitations for duration of 100 s. The infrared camera is placed to capture the temperature over the test sample at a distance of one meter from the sample and the temporal temperature distribution is recorded at a frame rate of 25 Hz. The mean rise in temperature profile during the active heating is removed by proper polynomial fit from the captured thermographic sequence. The frequency domain phase images have been constructed by performing the Fourier transform on reconstructed zero mean temporal temperature distribution of each and individual complimentary sequence is depicted (not shown). Further for each and individual mean removed thermographic sequences, the correlation coefficient between temporal temperature profile of each pixel with the chosen reference non-defective pixel is obtained is depicted (not shown). The frequency domain phase for the auto correlation sequences of individual complementary codes and their sum are computed.

In order to test the defect detection capabilities of the proposed approach, experiments and post processing has been carried out as explained in the above experimentation and data processing section for the mild steel and CFRP specimen. The results obtained for the steel sample of thickness is 9.74 mm, contains six flat bottom hole defects each of diameter 10 mm located at various depths (not shown), illustrate the acquired phase grams using Golay complementary code pair (a and b) respectively. The chosen phase grams for sequence a corresponds to 0.15 Hz and for sequence b corresponds to 0.21 Hz. The phase gram obtained at a frequency of 0.15 Hz from the sum of compressed pulses of sequence a and b. It can be visualized from the obtained results that detection capability of correlation sum phase gram gives better contrast compared to the individual sequence phase grams. Further, the suitability of the proposed post processing approach for the GCTWI has been applied to a rectangular shaped (151*341 mm) CFRP sample with 4.2 mm thickness containing blind holes and metallic inclusions as subsurface defects. The test sample contains two groups of defects having various diameters kept at the different depths. Group 1 contains a, b, c & d blind hole defects kept at 1.6 mm depth whereas group 2 contains e, f, g, h & i blind holes and inclusions type defects kept at 2.16 mm depth from the front surface of the sample. Defects e, f, and h (inclusions) are introduced as metallic backing of copper-covered steel (not shown). The acquired phase grams using Golay complementary code pair (a and b) respectively is illustrated (not shown). The chosen phase grams for sequence a and for sequence b correspond to 0.01 Hz. The phase gram obtained at a frequency of 0.03 Hz from the sum of compressed pulses of sequence a and b is presented (not shown).

The obtained phase grams (not shown) from the (a) sequence a (Phase 1), (b) sequence b (Phase 2) and (c) from the sum of compressed pulses of sequence a and b (Phase 3) is illustrated (not shown). Further a quantitative comparison of the detection capabilities of phase grams of the individual code and of the correlation sum is carried out by calculating signal to noise ratio (SNR) value as:

$$SNR_{(dB)} = 20 \log \frac{\text{Mean of the defective area} - \text{Mean of the nondefective area}}{\text{Standard deviation of the nondefective area}} \quad (10)$$

The obtained SNR values for each of the hidden defects considered for the mild steel and the CFRP samples (not shown). The results show that all the defects in both the materials (mild steel and CFRP) exhibit higher SNR in the correlation sum phase image compared to the obtained phase grams from the individual code sequences.

In exemplary embodiment, an overview on active thermographic excitation signals is described. Let a sinusoidal modulated signal s(t') used for exciting the incident heat flux in case of lock-in thermography is expressed as:

$$s(t')=a(t')\cdot\sin[2\pi f_c t'+\varphi(t')], \qquad (1)$$

where t' is the time [s], a(t') is the amplitude, fc is the carrier frequency [Hz] and φ(t') is the phase of the sinusoidal function of the above equation. The argument of sine in equation (1) is the phase function Φ(t') of the signal and it is given as:

$$\Phi(t')=2\pi f_c t'+\varphi(t') \qquad (2)$$

If φ(t') is a continuous time function, the time derivative of the phase is defined as the instantaneous frequency $f_i$:

$$f_i = \frac{1}{2\pi}\frac{d\Phi(t')}{dt'} = f_c + \frac{1}{2\pi}\frac{d\varphi(t')}{dt'} \qquad (3)$$

From equation (2) it can be seen that the phase modulation function has to be a non-linear function of time, since any linear term can be combined with a carrier frequency. If the amplitude a(t') varies slowly compared to the instantaneous frequency fi,|a(t)| represents essentially the envelope of the signal. The Fourier Transform of the signal s(t') (not shown) is denoted as S(f), f is denoting frequency [Hz]. s(t') and S(f) are related through the Fourier integrals.

$$S(f) = \int_{-\infty}^{+\infty} s(t')\cdot e^{-j2\pi ft'} dt' \qquad (4)$$

$$s(t') = \int_{-\infty}^{+\infty} S(f)\cdot e^{j2\pi ft'} df \qquad (5)$$

The energy (E) [J] of the signal is given by:

$$E = \int_{-\infty}^{+\infty} [s(t')]^2 dt' = \int_{-\infty}^{+\infty} |S(f)|^2 df \qquad (6)$$

where the second part of the equation is obtained by Parseval's equation:
Substituting equation (1) in equation (6), we obtain $$E = \frac{1}{2}\int_{-\infty}^{+\infty} [a(t')]^2 dt' + \frac{1}{2}\int_{-\infty}^{+\infty} [a(t')]^2 \sin\{2[2\pi f_c t' + \varphi(t')]\} dt' \qquad (7)$$

For narrow band excitation signals, in general the frequencies contained in the function a(t') and φ(t') are small compared to the carrier frequency fc. In this case, the second integral represents the oscillation of a sine under a slowly varying envelope and is essentially zero. Then, the energy can be approximated by:

$$\varepsilon \approx \frac{1}{2}\int_{-\infty}^{+\infty} [a(t')]^2 dt' \qquad (8)$$

This result shows that as to as the phase nodulation does not distort the signal envelope, the signal energy is not altered. The auto correlation function is defined by the integral:

$$R_{ss}(\tau') = \int_{-\infty}^{+\infty} s(t')s(t'-\tau')dt' = \int_{-\infty}^{+\infty} |S(f)|^2 e^{j2\pi f\tau'} df \qquad (9)$$

The auto correlation shows how different a signal is compared to it shifted version as a function of the time r', The maximum occurs when r'=0 (FIG. 1(b)) and is equal to the signal energy:

$$R_{ss,max}\Big|_{\tau'=0} = \int_{-\infty}^{+\infty} [s(t')]^2 dt' = E \qquad (10)$$

The excitation signals used in active thermography in practice are real, however the complex notation offers advantages particularly in expressing correlation integrals. The matched filter response for the obtained thermal profile is the key factor, computed with a suitable post-processing approach using correlation integrals for the coded excitation systems. Therefore, the use of complex notations is much more convenient. Since the spectrum of the real signal is symmetric around the zero frequency, an equivalent but simplified notation is a complex signal that has no zero frequencies and double the amplitude of the positive frequencies. A complex signal is called analytic if the spectrum consists of only positive frequencies. This is possible when the real and imaginary parts of the signal form a Hilbert pair. Let $$\psi(t')=\mu(t')\cdot e^{j2\pi f_c t'} \qquad (11)$$

be an analytic signal, whose real part is equal to the modulated signal in equation (1), μ(t') is a complex function with magnitude |μ(t')| and phase φ(t'), usually referred to as the complex envelope, and combines amplitude and phase modulation:

$$\mu(t')=|\mu(t')|\cdot e^{j\phi(t')}. \qquad (12)$$

The real waveform is derived as the real part of the complex signal:

$$s(t')=\text{Re}\{\psi(t')\}=|\mu(t')|\cdot\cos[2\pi f_c t'+\phi(t')] \qquad (13)$$

If Ψ(f) and M(f) art the Fourier Transform (FT) of the analytic signal ψ(t') and the complex envelope μ(t') respectively, the FT of equation (11) yields $$M(f)=\Psi(f+f_c). \qquad (14)$$

Thus, the frequency spectrum of the complex envelope is the shifted spectrum of the signal with a carrier frequency removed. When the real signal is narrow band the conditions:

$$a(t')\approx|\mu(t')|, \varphi(t')\approx\phi(t') \qquad (15)$$

are satisfied and the analytic complex signal is derived from the real signal simply by substituting the cosine with an exponent. Note that the resultant signal (sometimes referred to as exponential signal) will not be strictly analytic, if the fractional bandwidth of the real signal is so high, that the spectrum of the exponential signal falls over the negative frequencies. Using the second part of equation (6) and the fact that Ψ(f)=2S(f) for positive frequencies, the energy can now be written as:

$$E = \int_{-\infty}^{+\infty} |S(f)|^2 df = \int_0^{\infty} \left|\frac{1}{2}\Psi(f)\right|^2 df = \frac{1}{2}\int_{-\infty}^{\infty} |\Psi(f)|^2 df = \quad (16)$$

$$\frac{1}{2}\int_{-\infty}^{\infty} [\psi(t')]^2 dt' = \frac{1}{2}\int_{-\infty}^{\infty} |\mu(t')|^2 dt' = \frac{1}{2}\int_{-\infty}^{\infty} |M(f)|^2 df$$

The equality sign in the later part of equation (16) is exact, as opposite to the approximation in equation (8). This is another indication that going from real to the complex notation is only an approximation. In the rest of the analysis, it is assumed that the exponential signal is a good approximation of the analytic signal, an assumption that it is reasonable for the relatively narrow band signals that can excite the heat source. In a similar manner to the definition given in equation (9), the complex autocorrelation of $\psi(t')$ is given by:

$$R_{\psi\psi}(\tau') = \int_{-\infty}^{+\infty} \psi(t')\psi^*(t'-\tau')dt' = \int_{-\infty}^{+\infty} |\Psi(f)|^2 e^{j2\pi f\tau'} df. \quad (17)$$

Using equation (11) and equation (14), the auto correlation function can be expressed as a function of modulation:

$$R_{\psi\psi}(\tau') =$$

$$e^{j2\pi f\tau'}\int_{-\infty}^{+\infty} \mu(t')\mu^*(t'-\tau')dt' = e^{j2\pi f\tau'}\int_{-\infty}^{+\infty} |M(f)|^2 e^{j2\pi f\tau'} df \quad (18)$$

In an imaging system, the displayed quantity is the envelope of the signal. The envelope of the real auto correlation function is the matched-filter response, and it is in fact the inverse Fourier transform of the modulation's energy density spectrum $|M(f)|^2$:

$$Env\{R_{ss}(\tau')\} = \frac{1}{2}\left|R_{\psi\psi}(\tau')\right| = \quad (19)$$

$$\frac{1}{2}\left|\int_{-\infty}^{+\infty} \mu(t')\mu(t'-\tau')dt'\right| = \frac{1}{2}\left|\int_{-\infty}^{+\infty} |M(f)|^2 e^{j2\pi f\tau'} df\right|$$

The sketches (not shown) of the application of equation (19) in the estimate of the auto correlation envelope of a single-carrier pulse of length T' (not shown). In the absence of modulation, $\mu(t')$ is a real-valued rectangular window. The modulus of its FT M(f) is a sinc function (not shown), and the inverse FT of a sinc2 function is the triangle function (not shown).

This section deals with the applications of correlation integrals for widely used transient and steady-state active thermographic methods. The most popular active infrared thermographic techniques are pulse thermography, lock-in thermography, pulse phase thermography, frequency modulated thermal wave imaging, digitized frequency modulated thermal wave imaging and Barker coded thermal wave imaging. Among these methods, except PT, the most popular post-processing approach is the frequency domain phase extraction in order to detect sub-surface defects in the test specimen. The results obtained from this approach are insensitive to surface emissivity variations and nonuniform heating over the sample in addition to its deeper depth of penetration. In general, phase grams are reconstructed by applying the FT onto the captured thermos grams during the experimentation. These phase grams obtained at a particular frequency are used for detection of sub-surface defects. Due to the adopted frequency domain reconstruction process, the total supplied energy is redistributed to the individual frequency components. This disintegration of the supplied energy to individual frequency components under consideration, limits the applicability of the frequency domain data analysis schemes. In addition to this, phase gram obtained at a particular frequency limits the test resolution due to its fixed probing wavelength. These limitations can be overcome by considering the time-domain data processing schemes. Among the most widely used time-domain data processing schemes, this thesis concentrates mainly on matched filter based analysis. It is clear from the widely used thermal excitations such as lock-in thermography (not shown) and pulsed (pulse and pulse phase thermography) thermographic techniques (not shown) may not provide the energy concentration (compressed pulses) after correlating the temporal temperatures responses captured over the test specimen with respect to a chosen reference temporal thermal response (not shown). So the adopted correlation approach is not applied to these conventional thermographic techniques. This work mainly concentrates on pulse compression favourable thermal excitation schemes rather the conventional thermal approaches. The matched filter approach is correlation-based post processing data analysis scheme. Due to its merits, such as, results obtained from this approach are immune to random noises generated during the experimentation such as multiplicative noises (nonuniform illumination, emissivity variation over the sample surface) as well as the additive noise generated in the detection process. The following sections deals with the applicability of the correlation based post processing schemes on various widely used active infrared imaging methods. The widely used excitation signals (not shown) to drive the heat sources in active thermography (Linear frequency modulated thermal excitation with frequency varying from 0.01 Hz-1 Hz for a duration of 100 s, Digitized frequency modulated thermal excitation (digitized version of linear frequency modulated thermal excitation with frequency varying as 0.01 Hz-1 Hz for 100 s duration), Barker coded thermal excitation with each on bit duration of 14.285 s and Gaussian weighted frequency modulated thermal excitation obtained by applying spectral reshaping with mean 50 and standard deviation 20 on the linear frequency modulated thermal excitation) and their corresponding normalized auto-correlations (Pulse compressed thermal responses). It's clear for the aperiodic excitations the obtained auto-correlation function concentrates the supplied energy into a narrow duration high peak power virtual impulses (not shown). This improves the test sensitivity and resolution. These approaches are more prevalent in radar, sonar to enhance the range resolution with improved sensitivity even in a noisy environment. It allows the imposed heat flux using moderate peak power heat sources and produces the resolution and sensitivity similar to the results obtained with narrow duration high peak power impulse excitation.

Aperiodic thermal excitations (a). Linear frequency modulated with frequencies varying from 0.01 Hz-1 Hz for duration of 100 s (b). Digitized frequency modulated having fundamental frequencies varying from 0.01 Hz-1 Hz for duration of 100 s (c). Barker coded with each on bit duration of 14.285 s (d). Gaussian weighted with mean 50 and standard deviation 20 and (e). Auto correlation function of Linear frequency modulated thermal excitation (f). Auto correlation function of Digitized frequency modulated thermal excitation (g). Auto correlation function of Barker coded thermal excitation (h). Auto correlation function of Gaussian weighted thermal excitation respectively. Radio Detection And Ranging (RADAR) echoes from the targets can be considered as attenuated and delayed replicas of the corresponding transmitting signals due to reflection at target boundary. These electromagnetic waves propagate through free space as unguided transverse electromagnetic waves. They may not be influenced by dispersion, but affected by the relative moment of the target known as Doppler's effect, which results in an appreciable change in their operating bandwidth and centre frequency. Due to free space propagation they relatively have low attenuation. In general, these high frequencies with relatively large bandwidth producing sharp peaks in their correlation profiles, of whose peak delay is used to identify the range of the targets. However, in thermal wave imaging the obtained temperature profiles during the experimentation are heavily damped and delayed. Unlike radar, a non-zero mean offset may not be possible in thermal wave imaging due to successive cooling and heating of the sample (not shown). The mean increase in temperature during experimentation (not shown) makes this thermal wave imaging techniques to be considered as aperiodic thermal wave imaging methods. In order to apply the matched filter based signal/video processing techniques appropriate pre-processing (to reconstruct a zero mean temperature profile (not shown) has to be carried out to realize the merits of these aperiodic thermal wave imaging techniques on stationary aperiodic thermal profiles.

Figure 9:
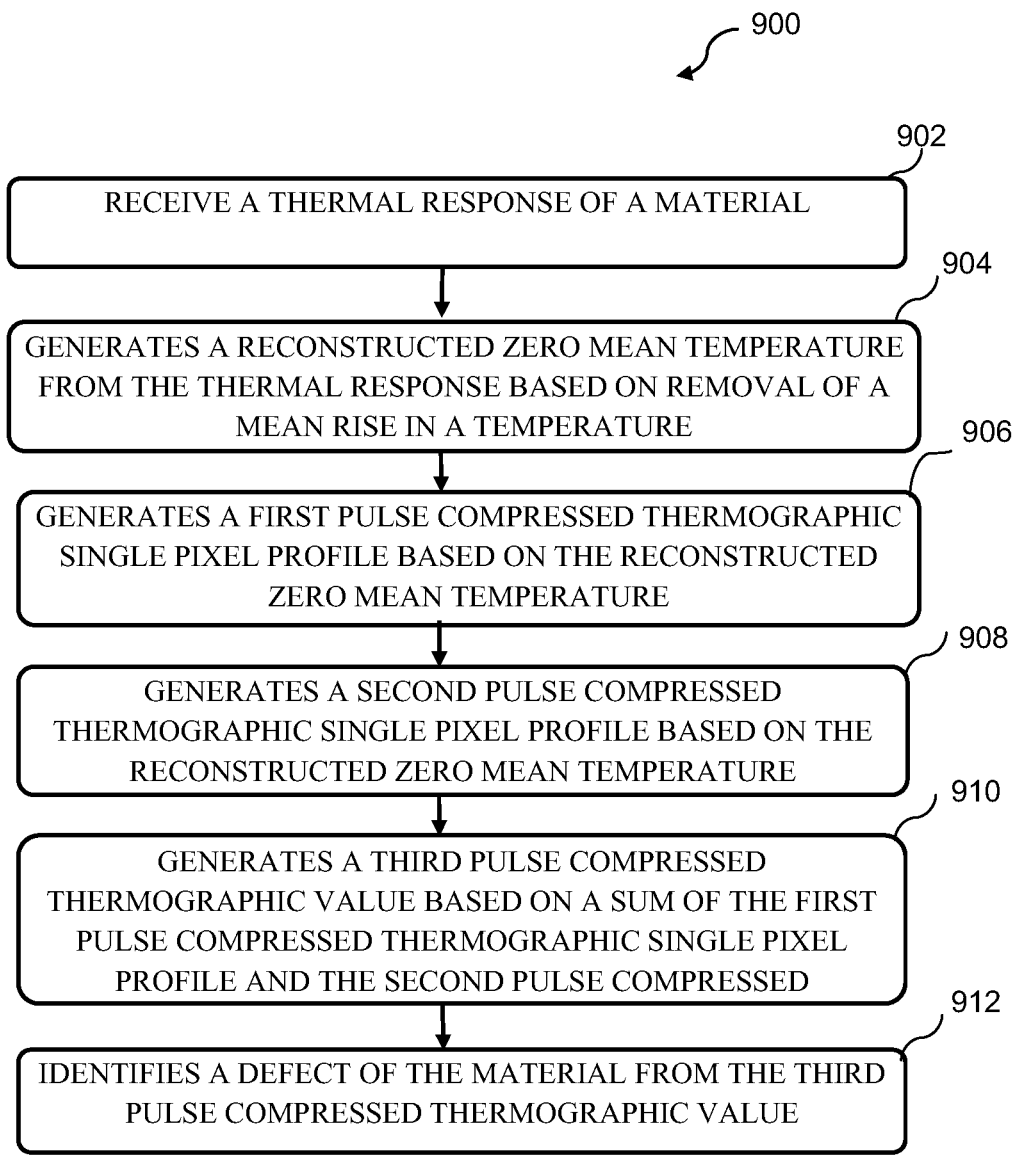
FIG. 9 illustrates a method of thermal imaging for identifying a defect in a material, in accordance with an embodiment of the present subject matter.

Further, referring to FIG. 9, a method of thermal imaging for identifying a defect in a material is illustrated. The order in which the method 900 is described is not intended to be construed as a limitation, and any number of the described method blocks can be combined in any order to implement the method 900 or alternate methods. Additionally, individual blocks may be deleted from the method 900 without departing from the spirit and scope of the subject matter described herein. Furthermore, the method 900 can be implemented in any suitable hardware, software, firmware, or combination thereof. However, for ease of explanation, in the embodiments described below, the method 900 may be considered to be implemented in the above described system 108.

At block 902, a thermal response of a material is received by the processor.

At block 904, a reconstructed zero mean temperature is generated from the thermal response based on removal of a mean rise in a temperature by the processor.

At block 906, a first pulse compressed thermographic single pixel profile is generated based on the reconstructed zero mean temperature.

At block 908, a second pulse compressed thermographic single pixel profile is generated based on the reconstructed zero mean temperature.

At block 910, a third pulse compressed thermographic value is generated based on a sum of an auto-correlation function of the first pulse compressed thermographic single pixel profile and the second pulse compressed thermographic single pixel profile.

At block 912, a defect of the material from the third pulse compressed thermographic value.

Exemplary embodiment may include an advantage. This may include the following.

In one embodiment there may include an advantage that includes the sensitivity for identifying the defect in the material 102 is improved by concentrating most of the supplied energy into a main lobe with reduced leakage into side lobes.

Although implementations for the system and method of thermal imaging for identifying the defect in the material have been described in language specific to structural features and/or methods, it is to be understood that the appended claims are not necessarily limited to the specific features or methods described. Rather, the specific features and methods are disclosed as examples of implementations for the system and method.

What is claimed is:

1. A method of thermal imaging for identifying a defect in a material, the method of thermal imaging for identifying the defect in the material comprises:
   receiving, by a processor (202), a thermal response of a material (102);
   generating, by the processor (202), a reconstructed zero mean temperature from the thermal response based on removal of a mean rise in a temperature;
   generating, by the processor (202), a first pulse compressed thermographic single pixel profile based on the reconstructed zero mean temperature;
   generating, by the processor (202), a second pulse compressed thermographic single pixel profile based on the reconstructed zero mean temperature
   generating, by the processor (202), a third pulse compressed thermographic value based on a sum of an auto correlation function of the first pulse compressed thermographic single pixel profile and the second pulse compressed thermographic single pixel profile; and
   identifying, by the processor (202), a defect of the material 102 from the third pulse compressed thermographic value.

2. The method as claimed in claim 1, wherein generating the reconstructed zero mean temperature from the thermal response based on removal of a mean rise in a temperature comprise the steps of:
   extracting, by the processor (202), a single pixel temperature profile from the thermal response;
   generating, by the processor (202), a zero mean single pixel profile based on applying a linear fit function on the single pixel temperature profile;
   storing, by the processor (202), the zero mean single pixel profile; and
   generating, by the processor (202), the reconstructed zero mean temperature from the zero mean single pixel profile.

3. The method as claimed in claim 1, wherein generating the first pulse compressed thermographic single pixel profile based on the reconstructed zero mean temperature comprise the steps of:
   extracting, by the processor (202), one pixel profile from the reconstructed zero mean temperature;
   generating, by the processor (202), a Fourier transform of the one pixel profile;
   generating, by the processor (202), a complex conjugate of the one pixel profile;
   extracting, by the processor (202), a second pixel profile from the reconstructed zero mean temperature;
   generating, by the processor, the Fourier transform of the second pixel profile;
   generating, by the processor (202), the first multiplied value based on multiplying the one pixel profile and the second pixel profile;
   generating, by the processor (202), an inverse Fourier transform of the first multiplied value; and
   generating, by the processor (202), the first pulse compressed thermographic single pixel profile from the inverse Fourier transform of the first multiplied value by extracting real components of the first multiplied value.

4. The method as claimed in claim 1, wherein generating the second pulse compressed thermographic single pixel profile based on the reconstructed zero mean temperature comprise the steps of:
extracting, by the processor (202), the third pixel profile from the reconstructed zero mean temperature;
generating, by the processor (202), a Fourier transform of the third pixel profile;
generating, by the processor (202), a complex conjugate of the third pixel profile;
extracting, by the processor (202), a fourth pixel profile from the reconstructed zero mean temperature;
generating, by the processor (202), the Fourier transform of the fourth pixel profile;
generating, by the processor (202), the second multiplied value based on multiplying the third pixel profile and the fourth pixel profile;
generating, by the processor (202), an inverse Fourier transform of the second multiplied value; and
generating, by the processor (202), the second pulse compressed thermographic single pixel profile from the inverse Fourier transform of the second multiplied value by extracting real components of the second multiplied value.

5. The method as claimed in claim 1, wherein generating the third pulse compressed thermographic value based on the sum of the auto correlation function of the first pulse compressed thermographic single pixel profile and the second pulse compressed thermographic single pixel profile comprise the steps of:
extracting, by the processor (202), a first single pixel pulse compressed profile from the first pulse compressed thermographic single pixel profile and a second single pixel pulse compressed profile from the second pulse compressed thermographic single pixel profile; and
generating, by the processor (202), the third pulse compressed thermographic value based on the addition of the first single pixel pulse compressed profile and the second pixel pulse compressed profile.

6. The method as claimed in claim 1, wherein the first pulse compressed thermographic single pixel profile is a golay sequence one.

7. The method as claimed in claim 1, wherein the second pulse compressed thermographic single pixel profile is a golay sequence two.

8. A system of thermal imaging for identifying a defect in a material, the system of comprises:
a memory (206);
a processor (202) coupled to the memory, wherein the processor is configured to receive a thermal response of a material (102), wherein the processor (202) is further configured to execute programmed instructions stored in the memory (206) for:
generating a reconstructed zero mean temperature from the thermal response based on removal of a mean rise in a temperature;
generating a first pulse compressed thermographic single pixel profile based on the reconstructed zero mean temperature;
generating a second pulse compressed thermographic single pixel profile based on the reconstructed zero mean temperature;
generating a third pulse compressed thermographic value based on a sum of an auto-correlation function of the first pulse compressed thermographic single pixel profile and the second pulse compressed thermographic single pixel profile; and
identifying a defect of the material (102) from the third pulse compressed thermographic value.

9. The system as claimed in claim 8, wherein the reconstructed zero mean temperature from the thermal response based on removal of a mean rise in a temperature comprises:
extracting a single pixel temperature profile from the thermal response;
generating a zero mean single pixel profile based on applying a linear fit function on the single pixel temperature profile;
storing the zero mean single pixel profile; and
generating the reconstructed zero mean temperature from the zero mean single pixel profile.

10. The system as claimed in claim 8, wherein generating the first pulse compressed thermographic single pixel profile based on the reconstructed zero mean temperature comprise the steps of:
extracting one pixel profile from the reconstructed zero mean temperature;
generating a Fourier transform of the one pixel profile;
generating a complex conjugate of the one pixel profile;
extracting a second pixel profile from the reconstructed zero mean temperature;
generating the first multiplied value based on multiplying the one pixel profile and the second pixel profile;
generating an inverse Fourier transform of the first multiplied value; and
generating the first pulse compressed thermographic single pixel profile from the inverse Fourier transform of the first multiplied value by extracting real components of the first multiplied value.

11. The system as claimed in claim 8, wherein generating the second pulse compressed thermographic single pixel profile based on the reconstructed zero mean temperature comprise the steps of:
extracting the third pixel profile from the reconstructed zero mean temperature;
generating a Fourier transform of the third pixel profile;
generating a complex conjugate of the third pixel profile;
extracting a fourth pixel profile from the reconstructed zero mean temperature;
generating the Fourier transform of the fourth pixel profile;
generating the second multiplied value based on multiplying the third pixel profile and the fourth pixel profile;
generating an inverse Fourier transform of the second multiplied value; and
generating the second pulse compressed thermographic single pixel profile from the inverse Fourier transform of the second multiplied value by extracting real components of the second multiplied value.

12. The system as claimed in claim 8, wherein generating the third pulse compressed thermographic value based on a sum of the auto-correlation function of the first pulse compressed thermographic single pixel profile and the second pulse compressed thermographic single pixel profile comprise the steps of:
extracting a first single pixel pulse compressed profile from the first pulse compressed thermographic single pixel profile and a second single pixel pulse compressed profile from the second pulse compressed thermographic single pixel profile; and generating the third pulse compressed thermographic value based on the addition of the first single pixel pulse compressed profile and the second pixel pulse compressed profile.

13. The system as claimed in claim 8, wherein the first pulse compressed thermographic single pixel profile is a golay sequence one.

14. The system as claimed in claim 8, wherein the second pulse compressed thermographic single pixel profile is a golay sequence two.

\* \* \* \* \*